United States Patent [19]

Schmidt et al.

[11] Patent Number: 5,413,102
[45] Date of Patent: May 9, 1995

[54] MEDICAL SENSOR

[75] Inventors: Michael Schmidt, Herrenberg; Malte Schlueter, Boeblingen, both of Germany

[73] Assignee: Hewlett-Packard Company, Palo Alto, Calif.

[21] Appl. No.: 245,665

[22] Filed: May 18, 1994

Related U.S. Application Data

[63] Continuation of Ser. No. 60,364, May 11, 1993.

[30] Foreign Application Priority Data

May 15, 1992 [EP] European Pat. Off. ............ 92108261

[51] Int. Cl.6 ............................................. A61B 5/00
[52] U.S. Cl. ..................................... 128/633; 128/666
[58] Field of Search .................................. 128/632–634, 128/664–667; 356/39–41

[56] References Cited

U.S. PATENT DOCUMENTS 5,249,576 10/1993 Goldberger et al. ............... 128/632

Primary Examiner—Angela D. Sykes

[57] ABSTRACT

A medical sensor for monitoring vital signs, in particular oxygen saturation, consists of a flexible carrier carrying the transmitter and receiver elements, and a housing element specifically adapted for application to a part of the human body, such as a finger. The flexible carrier may be used with a variety of different housing elements, such that it can be applied to virtually any limb or other part of the human body.

20 Claims, 5 Drawing Sheets

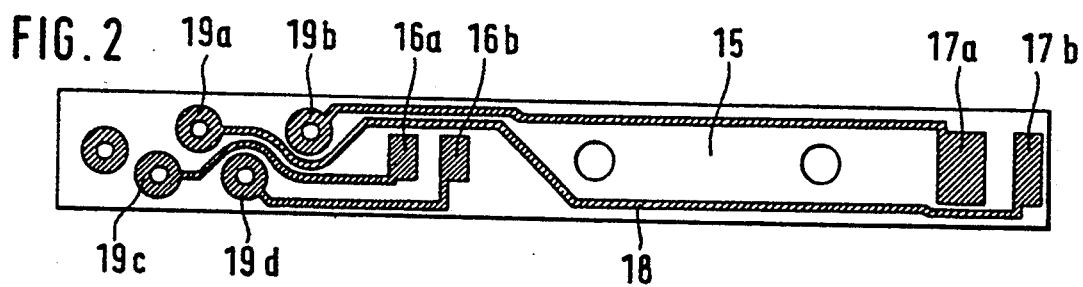
FIG. 2
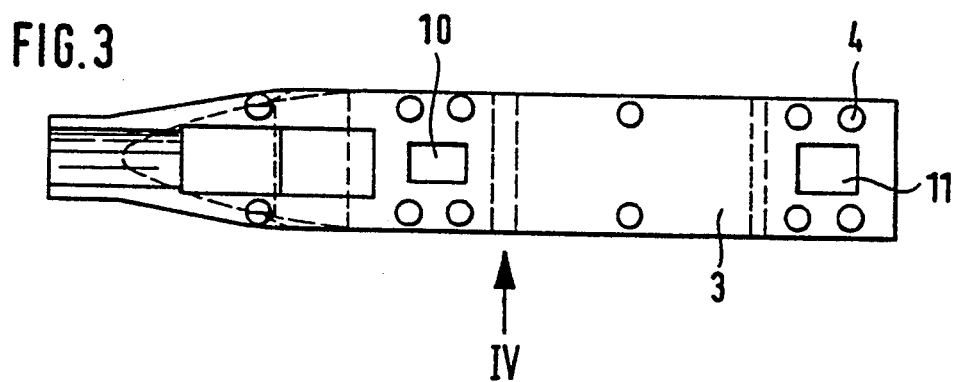
FIG. 3
FIG. 4
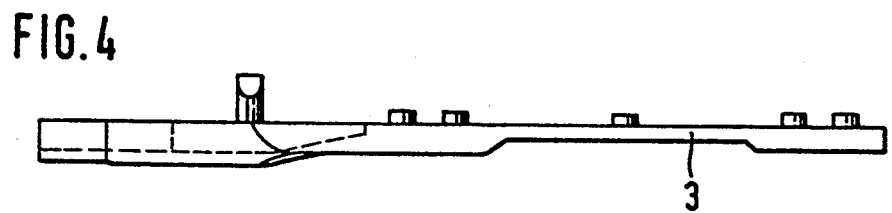
FIG. 5
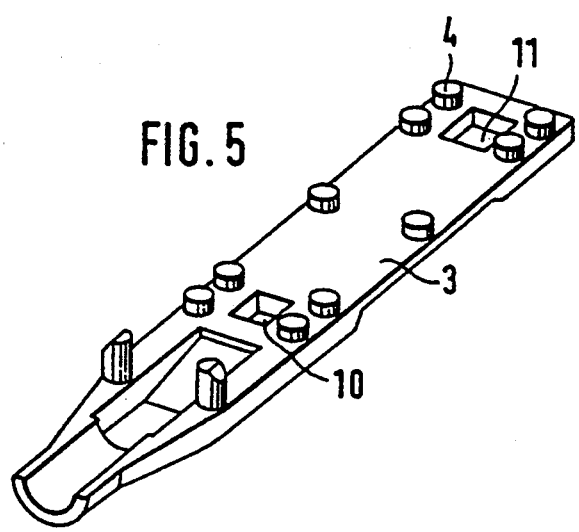

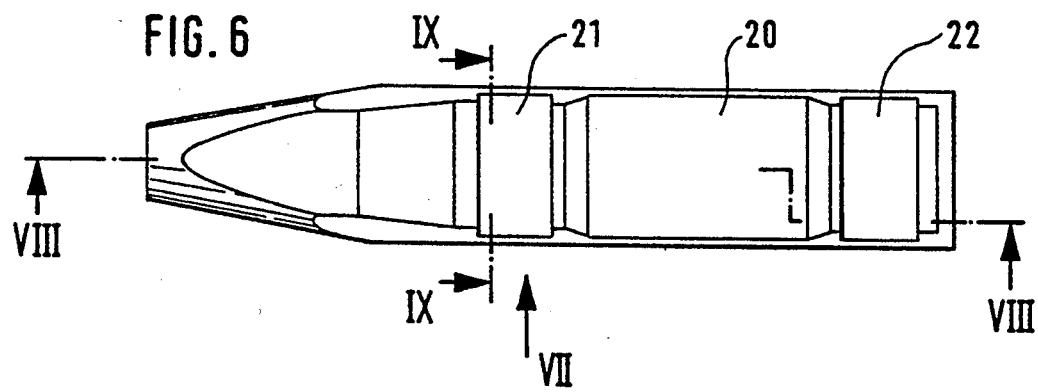
FIG. 6
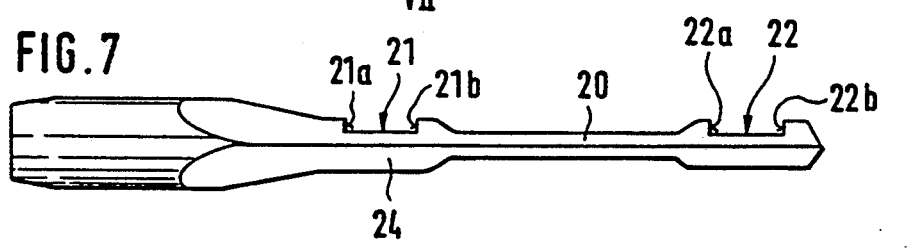
FIG. 7
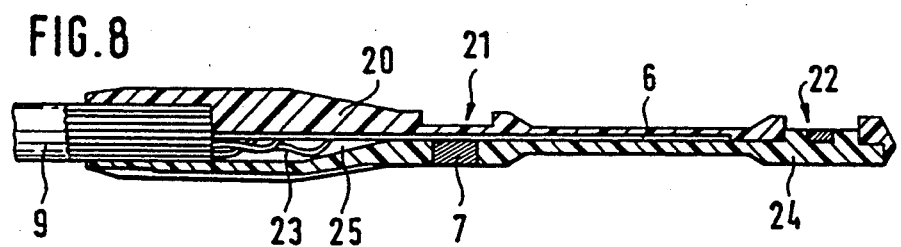
FIG. 8
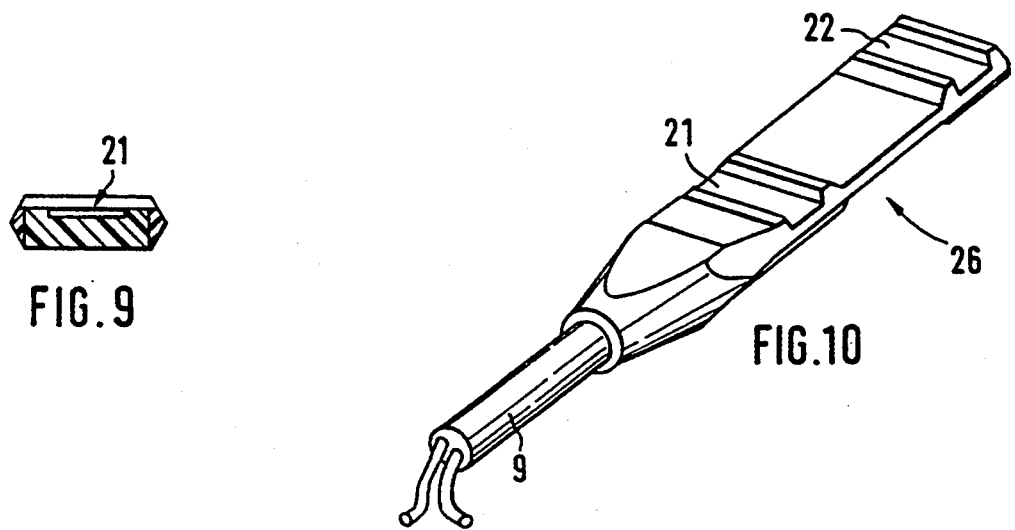
FIG. 9
FIG. 10

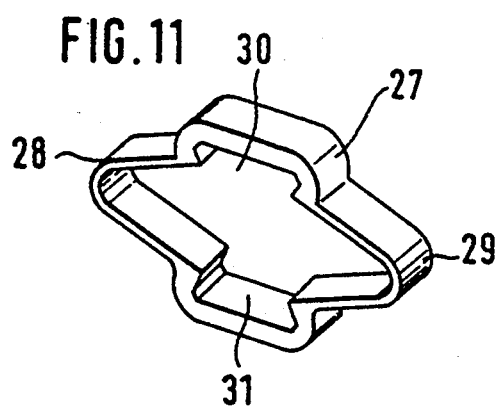
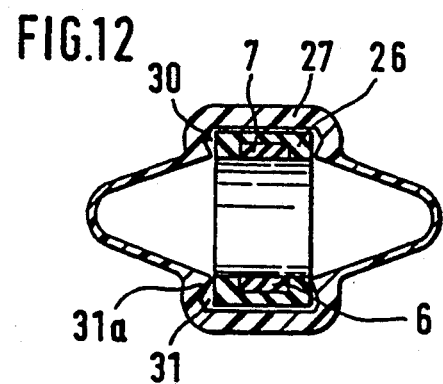
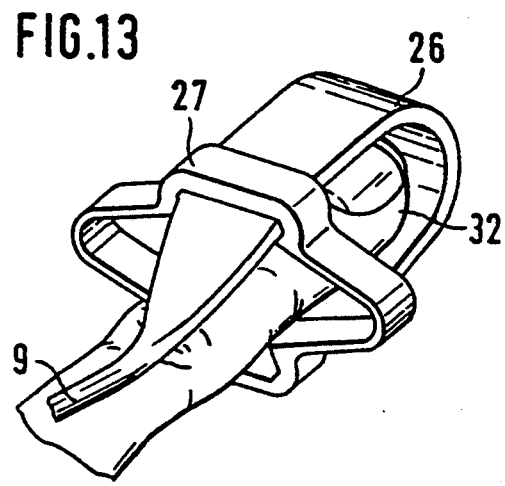
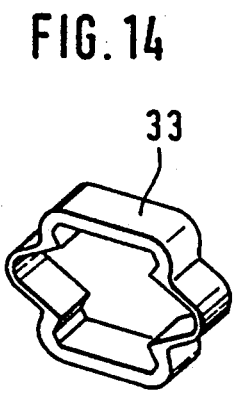
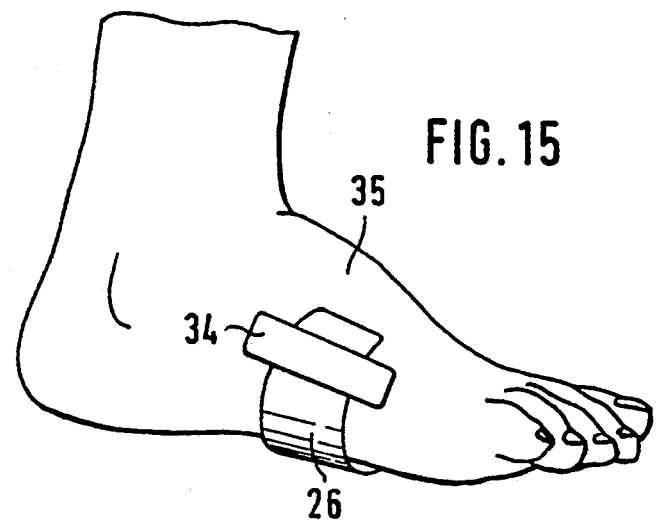

MEDICAL SENSOR

This is a continuation of application Ser. No. 08/060,364, filed May 11, 1993.

FIELD OF THE INVENTION

The present invention relates to the field of medical monitoring by electromagnetic waves transmitted through or reflected by human tissue. An electromagnetic wave, typically in or near the spectrum of visible light, can be irradiated by appropriate transmitters (e.g. optical transmitters in the visible or infrared spectrum) into human tissue, and the wave reflected by or transmitted through the tissue can be recorded by appropriate detectors. The received signal is useful for determination of a variety of physiological parameters, such as pulse or perfusion. A field of particular interest is pulse oximetry, i.e., measurement of oxygen saturation of the blood.

The present invention deals with a sensor suited to monitor vital signs of the kind discussed above, and a manufacturing method therefor.

BACKGROUND OF THE INVENTION

Sensors for trans-illuminating human tissue, or for recording illumination reflected by human tissue, in particular for pulse oximetry, have to fulfill several demands. The most important one is surely that the sensor has to provide a high quality physiological signal, in order to produce accurate readings. Thus, good skin contact, as well as immunity against patient movement, is required. The sensor should also provide sufficient comfort for the patient, i.e., it should not impair his well-being. Last, but not least, easy handling by medical personnel has to be ensured.

Apart from these physiological and medical considerations, the sensor should be easy to manufacture, at reasonable costs.

There have been several attempts in the prior art to fulfill the above needs. DE-A-37 03 458 discloses an elastic, self-contained sensor for application to a human finger. Another solution, also for application to a human finger, is discussed in U.S. Pat. No. 4,685,464. The latter document describes a sensor of the clothes-peg type.

There have also been prior art sensors which could be secured to the human skin by an adhesive. Such a sensor is disclosed in U.S. Pat. No. 4,830,014.

One will note that all of the above medical sensors are designed for application to a specific limb or other part of the human body. So far, the prior art sensors have revealed acceptable results.

However, one serious disadvantage of the prior art sensors (in particular, in terms of cost) is the above discussed aspect that different sensors have to be provided for different sites of application. The variety of different sensors necessitates intensive store-keeping, as a multiplicity of sensors have to be taken on stock. Another aspect is that different sensors require different product runs and are thus not as cheap to manufacture as would be the case if only a single sensor, with the associated number of pieces, would be manufactured. There are also clinical aspects which would make it desirable to have a single sensor only, instead of a variety of different sensors. For example, a patient may be monitored with a foot sensor, but it is desired, in the course of medical treatment, to continue monitoring with an ear sensor. In such a case, the foot sensor has to be completely removed and disconnected from the monitor; similarly, the ear sensor has to be applied, fastened, and connected to the monitor. Alarms have to be disabled during this process in order not to generate an alarm when the foot sensor is removed.

Another clinical problem in this context is that medical personnel have to be trained to use and apply all different kinds of sensors correctly. This is of particular importance in order not to miss any dangerous condition, e.g., a stress situation, of a patient.

The underlying problem becomes even more apparent in respect of disposable sensors, such as adhesive ones. If a patient is monitored at various different locations of the body, several sensors will have to be used, which are all thrown away afterwards.

It would therefore be desirable to have one common sensor for all of the various places of application. However, the prior art could not provide any solution. Therefore, as the sensors have necessarily to be adapted to the shape or geometry of the human skin at the place of application, in order to ensure tight contact with the skin. For example, a self-contained sensor of the type disclosed in DE-A-37 03 458 (which is intended for application to a human finger) cannot be applied to the human ear, or the human foot. Likewise, a sensor of the clothes-peg type (U.S. Pat. No. 4,685,464) cannot practically be applied to a foot (unless it is applied to a toe which is not a preferred location). Similar considerations apply when comparing sensors intended for use with an adult person to sensors intended for neonates.

SUMMARY OF THE INVENTION

It is thus a major object of the present invention to provide a concept for sensors of the kind described above which can essentially be used at different locations of the human body. A medical sensor according to the invention basically comprises:

flexible carrier means carrying at least one transmitter element and one receiver element;

a housing element for application to a part of the human body; and connection means for connecting the flexible carrier means and the housing element.

Advantageously, the transmitter element and the receiver element will be optical elements, in particular transmitter LEDs (light-emitting diodes), and receiver photodiodes or phototransistors. Such elements can be easily incorporated in the flexible carrier. One basic underlying idea of the present invention is that this flexible carrier is provided for all, or at least a considerable number of, places of application of interest. A housing element is provided which is specifically designed for application to a specific location, such as the finger. In other words, the housing element is specific to the place of application, whereas the flexible carrier means is not.

Further, connection means are provided for the interconnection of the flexible carrier and the housing element. The flexible carrier may, for example, be clipped onto or into the housing element. Other possibilities for connection of the two elements are the provision of an undercut, or recesses provided in the flexible carrier and/or the housing element. In one preferred embodiment of the present invention, the housing element includes one or more recesses with elastic side walls, such as would be the case if the housing element is manufactured from plastic material. The side walls may, in addition, comprise projections, such that a snap-on connection is established. However, it will be appreciated that recesses may also be provided in the flexible carrier instead, or that both the housing element and the flexible carrier may include recesses.

Another method of connecting the flexible carrier and the housing element is the provision of respective studs/buttons and holes, wherein the studs may either be part of the housing element, or of the flexible carrier.

Various housing elements, for application to different locations at the human body, may be provided. For example, in an advantageous embodiment of the present invention, the housing element includes a self-contained elastic clip. The connection means (e.g., the recesses), are provided at the inner surface of the clip. Such a housing element, as it will be discussed in more detail in conjunction with the drawings, is particularly suited for application to the finger of an adult person, or to the arm of a neonate.

In another preferred embodiment of the invention, the housing element includes an elastic clamp, wherein the connection means are provided at the inner surfaces of longitudinal projections of the elastic clamp. Such a housing element is particularly suited for application to the human ear. In case an additional hook or projection is provided, the housing element may be easily "snapped" into the auricle (external ear).

The above described design of a medical sensor according to the invention has several related advantages. In particular, it is easy to change the place of application. For example, a patient may be monitored at a finger, and it is intended to continue monitoring with an ear sensor. In such a case, the flexible carrier means is simply removed from the housing element which establishes contact to the finger, and connected with a different housing element intended for ear application. The electrical connections do not have to be released during this process, and the configuration of the monitor (such as alarm control) does not have to be modified. Thus, handling becomes quite easier.

The invention has also manufacturing and cost aspects. Manufacturing of a housing element is quite simple; for example, the housing element may be a component manufactured by injection molding. In contrast, manufacturing of the flexible carrier (which includes the optical elements and their interconnecting leads) is more expensive. In this respect, it is advantageous to have only one flexible carrier suited for connection with a variety of differently-shaped housing elements. Thus, a single flexible carrier may be used together with multiple housing elements. As the flexible carrier is more expensive, as compared to the housing element, this measure helps to save costs (in particular, if compared with prior art sensors wherein the optical elements had to be provided in each and every sensor). From the manufacturing standpoint, the provision of a single, unique flexible carrier is also of advantage, as only one single type of carrier has to be provided. This means, for example, that only one tool for manufacturing of the flexible carrier means has to be provided, and this further helps to save costs.

Another aspect is that the more expensive components, namely the flexible carrier, can be designed for multiple use. It should be noted that the housing element (which is cheap and easy to manufacture) can in fact be a disposable element connectable with the multi-use flexible carrier. If such a sensor has been used, only the housing element will be thrown away, whereas the flexible carrier is available for further use. Thus, none of the electronic or optic components is thrown away, which has not only cost advantages, but also helps to protect the environment.

In one preferred embodiment of the present invention, the flexible carrier means includes:
 a flexible layer to which the transmitter element and the receiver element is attached; and
 a flexible carrier body prepared for incorporating or mounting of the flexible layer.

This design makes interconnection of the transmitter element and the receiver element particularly easy, as the flexible layer may also include the electrical interconnections; preferably, the interconnections are copper leads (such that the flexible layer is basically treated as a printed circuit board). The flexible layer itself may advantageously be made from polyimide.

In another embodiment of the invention, the flexible carrier body discussed above comprises a lower body portion and an upper body portion, the lower body portion and the upper body portion being provided with body connection means, respectively, for interconnection of the two body portions. Interconnection is preferably provided by studs and respective openings. In this embodiment, the flexible layer is so-to-say "sandwiched" between the two body portions of the flexible carrier body and thus conveniently held and protected.

A preferred material for manufacturing the flexible carrier body, or the lower and/or upper portions thereof, is transparent plastic material which allows electromagnetic waves in or near the visible spectrum to pass. It has been found that transparent silicone particularly fits those needs.

The invention also relates to flexible carrier means for monitoring vital signs, in particular oxygen saturation, of a human being by means of electromagnetic waves transmitted through or reflected by human tissue, wherein the carrier means comprises:
 a flexible carrier body including a lower body portion and an upper body portion;
 body connection means for interconnection of the lower body portion and the upper body portion, preferably using studs and respective openings; a flexible layer to which at least a transmitter element and at least a receiver element is attached; and
 connection means for connecting the flexible carrier means with a housing element.

As already discussed, transparent plastics such as transparent silicone is particularly suited for manufacturing the lower and the upper body portions of the flexible carrier body. In this case, the body portions may advantageously be connected by plastic material, in particular colored silicone, which is injected in predefined recesses of either (or both) of the at least two body portions. It will be noted that such injection avoids any casting required in prior art technology to fix the electronic and optical components. The colored silicone is in particular injected into one or more recesses of the lower and/or the upper body portion, wherein the recess does not extend along or across the optical axes of the transmitter element and the receiver element, in order to allow the electromagnetic waves to pass.

As already discussed above, the present invention also relates to a housing element for a medical sensor which includes connection means for connecting the same with flexible carrier means. Preferred embodiments of such a housing element have already been disclosed at the outset.

Further, the present invention relates to a method for manufacturing flexible carrier means for monitoring vital signs, in particular oxygen saturation, of a human being by means of electromagnetic waves transmitted through or reflected by human tissue, the method comprising the steps of:

providing a lower body portion and an upper body portion of a flexible carrier body manufactured from transparent material, preferably transparent plastic material and in particular transparent silicone, wherein the lower body portion and the upper body portion are provided with respective body connection means;

providing a flexible layer to which a transmitter element and a receiver element are attached;

introducing the flexible layer between the lower body portion and the upper body portion of the flexible carrier body; and injecting plastic material, preferably silicone, and in particular colored silicone, in predefined recesses of the lower body portion and/or the upper body portion.

It is understood and expressly noted that the present invention relates to all useful and novel combinations of the above disclosed features, whether alone or in any other or arbitrary combination.

BRIEF DESCRIPTION OF THE DRAWINGS

The invention will now be explained, by means of a non-limiting example, with reference to the accompanying drawings, in which:

FIG. 2 is the top view of a flexible layer;

FIG. 3 is the top view of the lower body portion of the flexible carrier body;

FIG. 4 is a side view of the lower body portion in the direction of arrow IV of FIG. 3;

FIG. 5 is a perspective view of the lower body portion;

FIG. 6 is the top view of the assembled flexible carrier means;

FIG. 7 is a side view in the direction of arrow VII of FIG. 6;

FIG. 8 is a cross-section taken along the line VIII—VIII in FIG. 6;

FIG. 9 is a cross-section taken along the line IX—IX in FIG. 6;

FIG. 10 is a perspective view of the assembled flexible carrier means;

FIG. 11 shows a perspective view of a first housing element suited for application to a human finger;

FIG. 12 is a cross-section of the housing element shown in FIG. 11 with a flexible carrier means attached;

FIG. 13 is a perspective view of the housing element of FIG. 11 connected with a flexible carrier;

FIG. 14 is a housing element of similar structure as that shown in FIG. 11, but intended for neonatal application;

FIG. 15 depicts the application of a flexible carrier to a human foot;

DETAILED DESCRIPTION OF THE PREFERRED EMBODIMENTS

Figure 1:
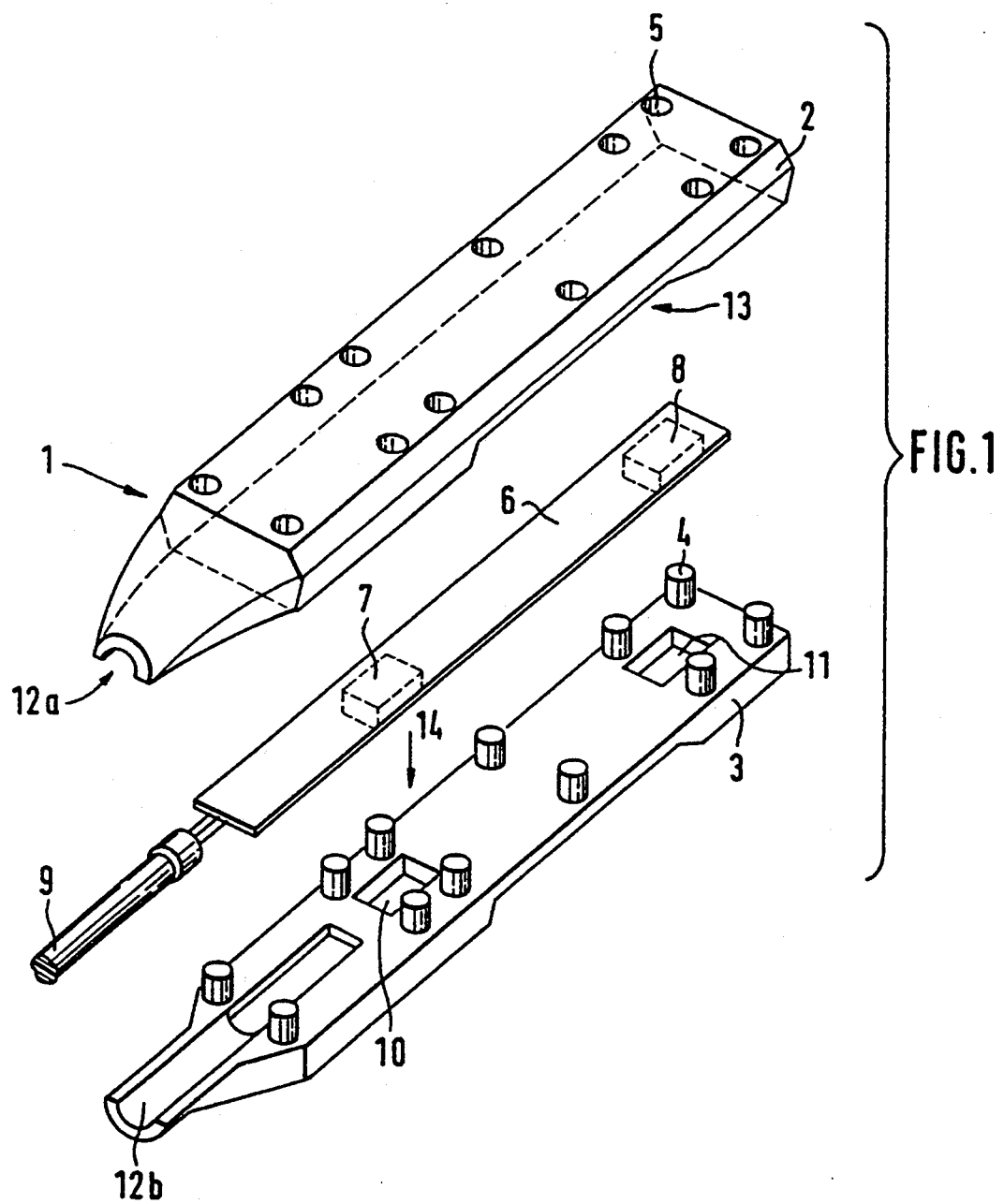
FIG. 1 depicts an exploded perspective view of flexible carrier means according to the present invention.

FIG. 1 depicts an exploded view of a flexible carrier generally outlined as 1. It consists basically of an upper body portion 2 and a lower body portion 3. Both portions 2 and 3 are manufactured from flexible, transparent silicone. Lower body portion 3 includes a multiplicity of projecting studs; by way of example, one of these studs is designated as 4 in FIG. 1. The studs engage with corresponding openings of the upper body portion, such as opening 5.

A flexible polyimide layer 6 carries a transmitter LED 7 and a receiver photodiode 8. Flexible layer 6 also includes copper leads (not shown in FIG. 1). These leads establish contact with a cable 9.

Upon manufacturing, flexible layer 6 is "sandwiched" between the two body portions 2 and 3. Optical elements 7 and 8 project into corresponding recesses 10 and 11 of lower body portion 3. Likewise, a cylinder-like recess (for cable 9) is provided in the two body portions (see references numbers 12a and 12b).

The assembly process includes more than the step of snapping upper body portion 2 onto lower body portion 3, thereby sandwiching flexible layer 6. Further, colored silicone is injected in predefined recesses, such as recess 13 of upper body portion 2, wherein the recesses do not cross the optical paths of elements 7 and 8 (transmitter element 7 radiates in the direction of arrow 14). When the colored silicone hardens, its surface interlaces or polymerizes with the transparent silicone material of body portions 2 and 3, thus ensuring a tight connection of the components shown in FIG. 1.

After manufacturing, carrier 1 is a highly-flexible element which can be connected, via cable 9, with an appropriate monitor. Preferably, carrier 1 is used for pulse oximetry purposes.

FIG. 2 depicts the top view of a flexible layer 15 of slightly different geometry than the flexible layer shown in FIG. 1. Layer 15 in FIG. 2 provides two transmitter elements 16a and 16b, as well as two receiver elements 17a and 17b. These are connected, via appropriate copper leads (such as copper lead 18), with pads 19a–19d. The single leads of cable 9 (FIG. 1) are soldered to these pads.

It will be appreciated that the number of transmitter and receiver elements is arbitrary. In particular, multiple transmitter elements (transmitting at different wavelengths) may be provided.

FIGS. 3–5 shows respective views of a lower portion of the flexible carrier body (manufactured from transparent plastic material as well), namely from the top (FIG. 3), from the side (FIG. 4), and a perspective view (FIG. 5). These views depict again the studs (such as stud 4) for connection of the upper body portion, as well as recesses 10 and 11 intended to house the optical elements.

FIGS. 6–10 depict various views and sections of the assembled flexible carrier. FIG. 6 is a top view, FIG. 7 a side view (see arrow VII in FIG. 6), and FIG. 10 is a perspective view. Likewise, FIGS. 8 and 9 are respective sections taken along lines VIII—VIII and IX—IX in FIG. 6.

One important feature of the upper body portion 20 are recesses 21 and 22. These recesses are provided for connection of the flexible carrier to various housing elements. The connection may either be performed by simply wedging or clamping recesses 21 and 22 to appropriate recesses of the housing element. A reliable connection is particularly obtained if the side walls of recesses 21 and 22—such as side walls 21a and 21b, and 22a and 22b in FIG. 7—are of elastic nature, such as is the case if upper body portion 20 is manufactured from transparent silicone (see discussion above). The facing side walls 21a–21b and 22a–22b may also be slightly inwardly inclined toward each other, in order to provide better contact.

FIG. 8 further depicts transmitter element 7, as well as the electrical leads (such as lead 23) connecting flexible layer 6 with cable 9. The lower body portion is outlined as 24 in FIGS. 6–10.

It will be noted that details of the mechanical construction in FIGS. 6–10 are slightly different than in the exploded view of FIG. 1.

It will be appreciated that other connection means for interconnection of the flexible carrier and a housing element may also be provided. In particular, a button and a respective button hole may be provided; this embodiment has the particular advantage that the two elements may be rotated with respect to each other. Undercuts, or similar solutions, may be provided as well.

FIG. 10 depicts the assembled flexible carrier 25 as a whole in perspective view. The recesses between upper body portion 20 and lower body portion 24 (such as recess 25) have been filled with colored silicone material, such that the opaque silicone interlaces with the transparent silicone material used to manufacture upper body portion 20 and lower body portion 24.

The completely assembled flexible carrier 26 is shown in perspective view in FIG. 10. The resulting carrier is completely flexible and may, for example, be bent over for connection to a housing element, as will be described later.

A first housing element 27 made from elastic plastic material is shown in FIG. 11. The structure of element 27 is closed in itself and intended for application to a finger of an adult person. Segments 28 and 29 of the closed contour provide sufficient flexibility for application to fingers of different diameter such as in DE-A-37 03458.

Two recesses 30 and 31 are provided for snap-in connection of a flexible carrier, such as carrier 26 in FIG. 10. The flexible carrier is bent over, with recesses 21 and 22 at the outside, and the flexible carrier is snapped into housing element 27 in a position wherein the flexible carrier is rotated around 90°, with respect to the housing element. Recess 21 of flexible carrier 26 thereby engages with recess 30 of housing element 27; similarly, recess 22 engages with recess 31. The medical sensor such assembled is shown in perspective view in FIG. 13. This figure also depicts the application of the assembled sensor to a human finger 32. It can be seen that flexible carrier 26 is held such in housing element 27 that the optical elements are automatically aligned on a common axis, such that the receiver element receives all radiation transmitted by the transmitter element through the human finger.

FIG. 12 depicts a cross-section through the assembled medical sensor. This figure depicts particularly that the side walls of recesses 30 and 31 are inclined, such as side wall 31a, in order to provide a reliable snap-on connection.

A second housing element 33 is shown in FIG. 14. This housing element is intended for neonatal application, e.g. for application to the finger of a critically ill baby. It will be noted that the outer shape of housing element 33 is quite similar to that of housing element 27 (FIGS. 11–13), but that the dimensions are smaller. Still the same flexible carrier may be used for adult housing element 27 and neonatal housing element 33.

Application of the flexible carrier 26 alone (i.e., without housing element) is shown in FIG. 15. In this case, the flexible carrier is attached with a plaster 34 to a human foot 35. A similar plaster, not shown in FIG. 15, is used to fix the lower portion of flexible carrier 26 to the bottom of foot 35, such that the optical elements incorporated in flexible carrier 26 oppose each other, for trans-illumination measurement.

Figure 16:
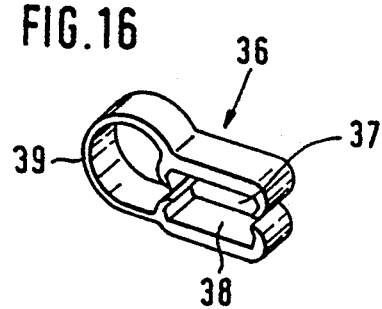
FIGS. 16 and 17 show respective housing elements in clamp-like form for application to the human ear.
Figure 18:
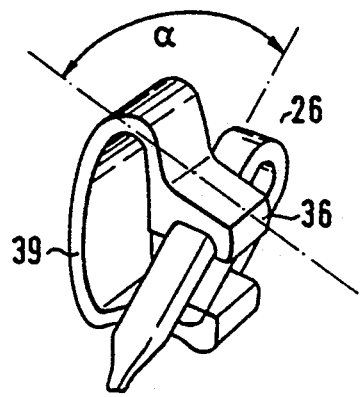
FIG. 18 shows another assembled ear sensor.

Yet another kind of housing element is shown in FIG. 16. Housing element 36 is intended for application to a human ear, in particular the lobe of the ear. Recesses 37 and 38 are provided for snap-in connection of flexible carrier 26, in a 90° angularly rotated position. The necessary tension is provided by the curved piece 39. FIG. 18 shows another, assembled ear sensor, wherein the angle α has been selected smaller than 90°, in order to make application easier.

Figure 17:
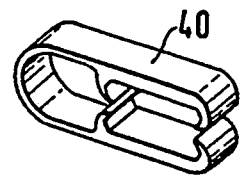

A similar ear sensor 40 is shown, in perspective view, in FIG. 17.

Figure 19:
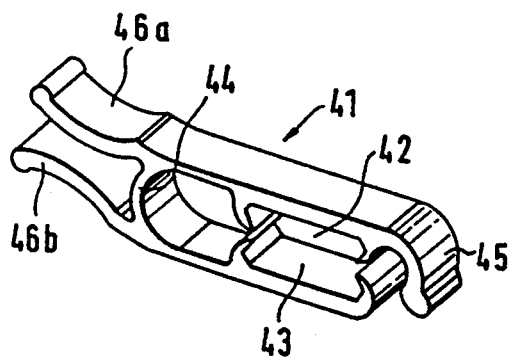
FIG. 19 depicts a housing element intended for application to the pinna, or the external ear.

FIG. 19 depicts another kind of ear sensor 41. The flexible carrier is snapped into recesses 42 and 43, as in the preceding examples. However, an additional hanger 45 is provided, for application to the external ear, such that the medical sensor is reliably kept at its place of application. Two clamp-like handles 46a and 46b make handling easier.

Figure 20:
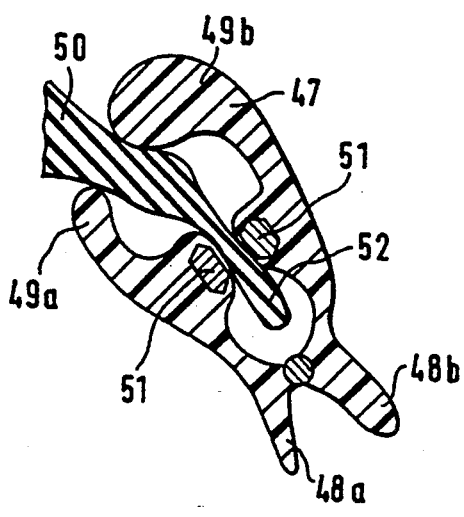
FIG. 20 shows a cross-section of another ear sensor.

Yet another type of ear sensor is shown in the cross-section of FIG. 20. Housing element 47 is of the clamp type and provides two handles 48a and 48b. Two projections 49a and 49b abut against the pinna or external ear 50 and thus hold the sensor reliably. The flexible carrier 51, however, abuts against the lobe of the ear 52. Thus, no pressure is exerted on the lobe of the ear 52, such that the lobe is fully perfused and therefore delivers accurate oxygen readings.

Figure 21:
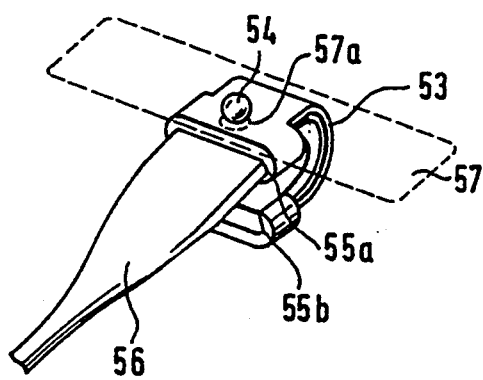
FIG. 21 depicts yet another embodiment of an ear sensor, e.g., for neonatal application.

Yet another type of housing element 53 is shown in FIG. 21. This housing element provides an additional knob or button 54, for easy application. Recesses 55a and 55b are similar to those already discussed above. The flexible carrier 56 is applied such that it adjoins or "docks" to the inner surface of housing element 53 (or, in other words, with an offset angle of 0°). The assembled sensor by be used for neonate monitoring, e.g., for appliance to an arm of the baby, and it may additionally be secured by means of a plaster, as indicated by the dotted structure 57 (with an additional hole 57a for knob 54).

What is claimed is:

1. A medical sensor for monitoring vital signs of a human being by means of electromagnetic waves transmitted through or reflected by human tissue, said medical sensor comprising:
    flexible carrier means carrying at least one transmitter element and one receiver element;
    a separate housing element specifically adapted for application to a part of the human body; and
    releasable connection means for releasably connecting together said flexible carrier means and said housing element, said housing element shaping said flexible carrier means into a configuration for effective monitoring of vital signs at said human body part.

2. Medical sensor according to claim 1, wherein said flexible carrier means includes:
   a flexible layer to which said transmitter element and said receiver element is attached; and
   a flexible carrier body for carrying said flexible layer.

3. The medical sensor according to claim 2, wherein said flexible layer is made from polyimide.

4. The medical sensor according to claim 2, wherein said flexible layer comprises conductive leads with contact pads for interconnection of said transmitter element and said receiver element.

5. The medical sensor according to claim 2, wherein said flexible carrier body comprises:
   a lower body portion; and
   an upper body portion; whereby
   said lower body portion and said upper body portion are provided with body connection means for interconnection of said lower body portion and said upper body portion.

6. The medical sensor according to claim 1, wherein said transmitter element and said receiver element are optical elements.

7. The medical sensor according to claim 8, wherein said transmitter and receiver elements are, respectively, a transmitter LED and a receiver photodetector.

8. The medical sensor according to claim 1 adapted for monitoring oxygen saturation of a human body part.

9. The medical sensor according to claim 1, comprising a kit of housing elements, each said housing element in said kit specifically adapted for application to a different part of the human body, said flexible carrier means defining a universal flexible carrier body which can be connected to any one of said housing elements in said kit.

10. A flexible carrier device for monitoring vital signs of a human being by means of electromagnetic waves transmitted through or reflected by human tissue, said flexible carrier device comprising:
    a flexible carrier body including a lower body portion and an upper body portion;
    body connection means for interconnection of said lower body portion and said upper body portion;
    a transmitter element and compatible receiver element;
    a flexible layer to which at least said transmitter element and at least said receiver element are attached; and
    releasable connection means for releasably connecting said flexible carrier device with a separate housing element and conforming said flexible carrier device to a desired shade supported by the housing element.

11. The flexible carrier device according to claim 10, wherein said body connection means is of plastic material.

12. The flexible carrier device according to claim 11, wherein said plastic material is colored silicone.

13. The flexible carrier device according to claim 10, wherein said flexible layer is made from polyimide.

14. The flexible carrier device according to claim 10, wherein said flexible layer comprises conductive leads with contact pads for interconnection of said transmitter element and said receiver element.

15. The flexible carrier device according to claim 10 adapted for monitoring oxygen saturation of a human body part.

16. The flexible carrier device according to claim 10, wherein said releasable connection means releasably connects said flexible carrier device to any one of a plurality of differently configured housing elements.

17. A housing element for use in a medical sensor for monitoring vital signs of a human being by means of electromagnetic waves transmitted through or reflected by human tissue, said housing element including releasable connection means for releasably connecting said housing element with a separate flexible carrier means, said housing element specifically adapted for shaping the flexible carrier means into a configuration for application to a part of the human body.

18. The housing element according to claim 17 having recesses defining said connection means.

19. The housing element according to claim 18, wherein said recesses have side walls having projections, in order to provide a snap-on connection.

20. The housing element according to claim 17, wherein said releasable connection means is specifically adapted to accommodate a universal flexible carrier means for a plurality of different configurations of said housing element.

* * * * *